United States Patent [19]

Horlenko et al.

[11] Patent Number: 4,480,122

[45] Date of Patent: Oct. 30, 1984

[54] PROCESS FOR PRODUCING METHYL FORMATE

[75] Inventors: Theodore Horlenko; Adolfo Aguilo, both of Corpus Christi, Tex.

[73] Assignee: Celanese Corporation, New York, N.Y.

[21] Appl. No.: 423,977

[22] Filed: Sep. 27, 1982

[51] Int. Cl.³ .................. C07C 67/40; C07C 69/06
[52] U.S. Cl. .................... 560/239; 502/346; 502/524
[58] Field of Search ............... 560/239; 502/524, 346

[56] References Cited

U.S. PATENT DOCUMENTS 1,975,853 10/1934 Lazier ............................ 560/239
4,149,009 4/1979 Yoneoka et al. ............... 560/239
4,232,171 11/1980 Yoneoka et al. ............... 560/239

*Primary Examiner*—Vivian Garner
*Attorney, Agent, or Firm*—L. I. Grim; M. Turken

[57] ABSTRACT

A process for producing methyl formate is described by the dehydrogenation of methanol over a catalyst produced by reducing a precursor comprising copper oxide and a spinel structure support comprising the oxides of zinc and aluminum, said precursor containing 10 to 80 percent copper.

7 Claims, No Drawings

PROCESS FOR PRODUCING METHYL FORMATE

PROCESS FOR PRODUCING METHYL FORMATE

This invention relates to a process for producing methyl formate by the dehydrogenation of methanol.

BACKGROUND OF THE INVENTION

It is known to make methyl formate, which has utility as a fumigant or as an intermediate for the production of formic acid, by the dehydrogenation of methanol. For example, British Pat. No. 1,546,004 describes a technique of carrying out the process using specific copper catalysts to provide good methanol conversions and highly selective methyl formate production. Some of the most effective catalysts for the reaction described in this patent are combinations of copper, zirconium and zinc and of copper, zirconium, zinc and aluminum. The combination of copper and zinc is also described as a catalyst for the methyl formate production from methanol but it appears that the conversion of the methanol and yields of methyl formate diminishes significantly after the operation is running for 50 hours. Other references disclosing this reaction are Japanese Patent Publication 53108916 which describes a copper, zinc and silica catalyst combination and Japanese Patent Publication No. 53068716 which describes a catalyst containing oxides of copper, chromium, manganese, magnesium and/or potassium. None of these references describe the catalyst used in the process of the present invention.

THE INVENTION

In accordance with this invention, there is provided a process for the vapor phase dehydrogenation of methanol to methyl formate over a catalyst produced by reducing a catalyst precursor comprising copper oxide in an amount such that said precursor comprises about 10 to 80 weight percent of copper based on the total metals present, with the balance essentially a spinel structure support comprising the oxides of zinc and aluminum. The spinel support structure and copper oxide are present in the form of crystallites no greater than 120 Angstrom units. The precursor is described in U.S. Pat. No. 3,923,694 entitled "Methanol Synthesis Catalyst" issued Dec. 2, 1975 to Cornthwaite and assigned to Imperical Chemical Industries. The entire disclosure of this patent relating to the precursor is hereby incorporated by reference. It is of specific interest that the catalyst used in this invention can be used in the dehydrogenation of methanol to methyl formate under conditions of atmospheric pressure or reduced pressures and has another use as a catalyst in the methanol production from synthesis gas at pressures as low as 50 atmospheres.

An example of a catalyst as used in this invention is the hydrogen reduced precursor as described in U.S. Pat. No. 3,923,694. The precursor comprises copper oxide and a support comprising the mixture of zinc oxide and aluminum oxide formed in a spinel structure characterized by the presence of spinel in crystallites not larger than 120 Angstrom units.

In preparing the catalyst used in this invention the precursor is reduced to provide an active catalyst in the presence of hydrogen by raising the temperature slowly to 250° C. and maintaining this temperature for six hours at 250° C. The amount of hydrogen used is controlled to prevent an exotherm of the reduction from exceeding the temperature which would alter or destroy physically the structure of the precursor.

In the catalyst precursor, the spinel crystallites are preferably not greater than about 80 Angstrom units and especially preferred are those which are about 30 to about 40 Angstrom units in size in any dimension. The copper oxide crystallites are preferably no greater than 120 Angstrom units, and particularly preferred are crystallites no greater than 70 Angstrom units in size in any dimension. The spinel and copper oxide crystallites are suitably in the form of short prisms, cubes, spheroids and spheres, i.e., non-elongated shapes. The catalyst precursor can be present in the form of pressed pellets or in the form of powder.

The techniques of measurement of crystallite size of the components of the catalyst precursor are described in U.S. Pat. No. 3,923,694.

The most significant measurement is the crystallite size (meaning the average length of crystallite) as determined by x-ray diffraction using the method described in Chapter 9 of "X-ray Diffraction Procedures" by H. P. Klug and L. E. Alexander, published by Chapman and Hall Limited, London 1954.

The method of making the catalyst precursor comprises the co-precipitation from aqueous solutions of thermally decomposable compounds of zinc and aluminum capable of forming together a mixed oxide having the spinel structure, precipitating the copper compounds from an aqueous solution in the presence of the first formed zinc and aluminum precipitate, washing the resulting whole precipitate and calcining it to give the metal oxides. This precursor is then reduced with hydrogen to give the active catalyst. After calcination the content of copper oxide is preferably 3 to 5 times by weight of the zinc oxide carried by the support.

The term "spinel structure" is known in the art as a group of minerals having the general formula $AB_2O_4$ where A is zinc and B is aluminum. The structure consists of cubic close-packed oxygen atoms with zinc and aluminum in 4-fold and 6-fold interstices respectively. To balance the electrical charges (eight negative charges are given by $O_4$), one divalent cation (zinc) and two trivalent cations (aluminum) are needed. The distribution of atoms depends on subtle chemical factors and on temperature. The spinel structure generally occurs as octahedral crystals, often exhibiting twinning. The amount of spinel structure in the support oxides of the precursor can be present from about 2 to about 20 weight percent, preferably about 10 weight percent of the support.

The support oxides of the precursor contain about 10 to about 60 weight percent of the total catalyst precursor, preferably about 15 to about 30 weight percent.

The copper content of the precursor catalyst ranges from about 10 to about 80 percent, preferably about 25 to about 70 percent based on the total metal atoms present in the precursor. When the copper is in this preferred range, the total zinc content ranges from about 0.3 to about 0.6 of the copper content based on metal atoms.

The dehydrogenation of methanol is carried out by contacting the catalyst with methanol in vapor phase at atmospheric pressure or reduced pressures. The reaction temperature can be in the range of from about 235° C. to about 350° C. preferably about 250° C. to about 320° C. The space time yield (STY) of the reaction ranges from about 500 to about 2200 grams product per liter reactor space per hour, at contact times (NTP)

ranging from about 0.3 to about 2.0 seconds, preferably from about 0.5 to about 1.5 seconds. The contact time (NTP) as used herein means the contact time adjusted to 25° C., and atmospheric pressure. The contact time is calculated by dividing the volume of the catalyst bed (including voids) by the volume per unit time flow rate.

The present invention is illustrated by the following examples:

EXAMPLES 1 THROUGH 9

The catalyst preparation was carried out in the manner described in the example of U.S. Pat. No. 3,923,694 to provide pellets of catalyst having the following composition by weight percent of the total metals:

| Metal[1] | Wt. %[2] |
|---|---|
| Copper | 40 |
| Zinc | 20 |
| Aluminum | 4 |

This corresponds to an atomic ratio of approximately $Cu_6Zn_{2.9}Al_{1.4}$ and contains spinel structures containing zinc and aluminum. The catalyst was crushed to $-20+30$ mesh size and placed in the reactor described below. Hydrogen was passed over the catalyst in a manner so that no significant exotherm occurred while heating the catalyst slowly to 250° C. After reaching 250° C., the temperature was maintained for six hours.

DEHYDROGENATION OF METHANOL TO METHYL FORMATE

After the catalyst was activated, methanol was pumped through a ¼ inch diameter (316 stainless steel) tube 6 inches long wherein the methanol was preheated. The preheated methanol was passed into a ⅜ inch diameter (316 stainless steel) electrically heated reactor tube 8 inches long (total volume 8 millimeters) and containing 7.6 millimeters activated and hydrogen reduced catalyst described above. The reactor tube contained a reactor skin temperature thermocouple located at the midpoint of the reactor and this thermocouple monitors the system. Once the desired feed rate was established, the reactor was allowed to stabilize. The system was considered stabilized when the temperature of the reactor skin temperature thermocouple is stable. The temperature of the system is controlled by adjusting the variac setting for electricity supplied to the reactor shell.

When the system was stabilized at the desired reaction temperature, a run was started by connecting dry ice traps to the system. A gas sample tube was placed between the last dry ice trap and a bubble meter. The reactor shell temperature was recorded at the beginning and end of the reaction run. The feed rate was checked and the dry vent gas through the dry ice traps was measured with a bubble meter. The run duration and product weight were recorded for use in material balance calculations. The gas sample was analyzed for hydrogen, carbon monoxide and carbon dioxide by a mass spectrometer. The liquid product was analyzed by flame ionization gas chromatography for methyl formate and the methanol was taken by difference. Preliminary analysis of the reaction liquid by mass spectrometer showed only methyl formate and methanol were present and only two peaks are obtained on the gas chromatography. Table I below describes the conditions and results of the methanol dehydrogenation process.

TABLE I

Dehydrogenation of Methanol to Methyl Formate

| Examples | Reactor Shell Temp. °C. | Methanol Feed Grams | Product Grams | Product Methyl Formate Wt. % | Total Vent Gas ml. | $H_2$ Produced Mole % | CO Produced Mole % | NTP Contact Time Sec. | Methanol Conversion % | % Methanol to Methyl Formate Efficiency | % Methyl Formate Yield | Space Time Yield Grams Product Per Liter Space Per Hour |
|---|---|---|---|---|---|---|---|---|---|---|---|---|
| 1 | 237 | 54.7 | 56.3 | 12.7 | 7945 | 91.5 | 7.4 | 0.7 | 14.6 | 91 | 13 | 807 |
| 2 | 222 | 46.9 | 44.2 | 8.6 | 3780 | 93.1 | 5.8 | 0.7 | 9.7 | 93 | 9 | 500 |
| 3 | 265 | 62.6 | 58.5 | 27.3 | 20800 | 90.6 | 8.3 | 0.7 | 31.2 | 88 | 28 | 1576 |
| 4 | 287 | 23.5 | 21.2 | 30.0 | 9390 | 89.4 | 9.5 | 0.7 | 34.9 | 85 | 30 | 1666 |
| 5 | 303 | 31.3 | 25.5 | 36.2 | 16200 | 86.3 | 12.3 | 0.7 | 43.4 | 79 | 34 | 2237 |
| 6 | 279 | 43.6 | 38.4 | 32.0 | 19670 | 91.9 | 7.0 | 1.4 | 36.4 | 88 | 32 | 844 |
| 7 | 255 | 36.0 | 34.1 | 21.0 | 8930 | 89.7 | 7.0 | 1.4 | 23.9 | 90 | 22 | 595 |
| 8 | 297 | 22.8 | 15.2 | 29.5 | 9660 | 73.4 | 22.3 | 1.4 | 41.5 | 63 | 26 | 590 |
| 9 | 227 | 26.5 | 25.8 | 4.5 | 1680 | 92.3 | 2.8 | 1.4 | 5.0 | 95 | 5 | 131 |

[1]Present as the oxide
[2]Weight of metal in oxide

Where methyl formate is produced from methanol, selectivity to methyl formate is relative to conversion of methanol. It is preferred to maintain the conversion of methanol at about 20 to about 60 percent in order to keep selectivity to methyl formate high.

EXAMPLE 10

For comparison with the catalysts of this invention described in Examples 1 through 9, catalysts containing copper, zinc, zirconium and aluminum were prepared in accordance with the general procedures described in Example 9 of British Pat. No. 1,546,004. Details of the two specific methods used for preparing the catalyst are given below.

METHOD A (1) Dissolve 101.6 grams copper nitrate $Cu(NO_3)_2.3H_2O$ in 400 milliliters water, heat to 70° C.
(2) Dissolve 39.3 grams zinc nitrate, $Zn(NO_3)_2.6H_2O$ in 200 milliliters water, heat to 70° C.
(3) Dissolve 65 grams anhydrous $Na_2CO_3$ in 600 milliliters water, heat to 70° C.
(4) Add solution 1 and solution 2 to solution 3, separately, slowly, with good stirring.
(5) Filter the resultant precipitate on a Buchner funnel, wash with water.
(6) Transfer the wet precipitate to a glass baking dish. Add 27.0 grams zirconium carbonate (hydrated) $[2ZrO_2.CO_2.7H_2O]$ plus 2.1 grams colloidal aluminum oxide ($Al_2O_3$). Mix the mass thoroughly by kneading with a spatula and spoon.

(7) Dry overnight at 70° C., then calcine at 390° C. for 2 hours.

(8) Compress the powder into a tablet one inch in diameter by ½ inch thick. Reduce to −20+30 mesh.

(9) Charge the reactor with 8 milliliters of catalyst and reduce in a stream of hydrogen at 200° C. for 6 hours. The catalyst produced is $CuZn_{0.3}Zr_{0.3}Al_{0.1}$.

The catalyst produced is $CuZn_{0.3}Zr_{0.3}Al_{0.1}$.

EXAMPLES 11 THROUGH 20

The catalyst of Method A in Example 10 having the metallic atomic ratio $CuZn_{0.3}Zr_{0.3}Al_{0.1}$ was placed in the same equipment and the same procedure was used as described in Examples 1 through 9 to produce methyl formate from methanol. Table II describes the conditions and results of the methanol dehydrogenation process.

TABLE II

Dehydrogenation of Methanol to Methyl Formate

| Examples | Reactor Shell Temp. °C. | Methanol Feed Grams | Product Grams | Product Methyl Formate Wt. % | Total Vent Gas ml. | $H_2$ Produced Mole % | CO Produced Mole % | NTP Contact Time Sec. | Methanol Conversion % | % Methanol to Methyl Formate Efficiency | % Methyl Formate Yield | Space Time Yield Grams Product Per Liter Space Per Hour |
|---|---|---|---|---|---|---|---|---|---|---|---|---|
| 11 | 330 | 27.4 | 12.0 | 12.0 | 33138 | 64.9 | 34.1 | 2.1 | 61 | 9 | 5 | 118 |
| 12 | 330 | 41.9 | 30.5 | 14.0 | 27755 | 64.7 | 34.3 | 1.4 | 39 | 27 | 11 | 342 |
| 13 | 330 | 38.9 | 35.6 | 13.2 | 10470 | 78.5 | 20.9 | 0.7 | 20 | 64 | 13 | 814 |
| 14 | 330 | 72.8 | 62.3 | 10.9 | 12090 | 73.3 | 25.6 | 0.4 | 17 | 64 | 11 | 1185 |
| 15 | 300 | 27.2 | 24.8 | 13.2 | 11214 | 70.9 | 28.3 | 2.1 | 26 | 45 | 12 | 270 |
| 16 | 300 | 39.1 | 36.4 | 12.4 | 9516 | 64.4 | 35.0 | 1.4 | 20 | 59 | 12 | 379 |
| 17 | 300 | 38.2 | 37.1 | 9.2 | 5160 | 82.9 | 16.0 | 0.7 | 12 | 77 | 9 | 597 |
| 18 | 280 | 26.7 | 23.9 | 11.9 | 6283 | 74.9 | 24.5 | 2.1 | 19 | 60 | 11 | 244 |
| 19 | 280 | 39.2 | 37.7 | 9.8 | 5940 | 83.4 | 15.6 | 1.4 | 13 | 77 | 10 | 321 |
| 20 | 280 | 38.2 | 37.0 | 6.9 | 3030 | 82.6 | 15.0 | 0.7 | 10 | 83 | 8 | 445 |

METHOD B (1) Dissolve 101.6 grams copper nitrate, $Cu(NO_3)_2.3H_2O$ in 400 milliliters water, heat to 70° C.

(2) Dissolve 49 grams anhydrous sodium carbonate, $Na_2CO_3$, in 400 milliliters water, heat to 70° C.

(3) Add solution 1 to solution 2 slowly while stirring, then continue stirring at 70° C. for 1½ hours.

(4) Remove solution 3 from hot plate and let stand for 1 hour at room temperature.

(5) Filter the precipitate in (4) on a Buchner funnel, wash with water.

(6) Transfer the wet precipitate of (5) to a glass baking dish. Add 27.6 grams zinc zirconate ($ZnZrO_3$) plus 2.1 grams of colloidal aluminum oxide ($Al_2O_3$). Mix the entire mass thoroughly by kneading with a spatula and spoon.

(7) Dry overnight at 70° C., then calcine 2 hours at 390° C.

(8) Compress the powder into a tablet one inch in diameter by ½ inch thick. Reduce to −20+30 mesh.

(9) Charge reactor with 8 milliliters of catalyst and reduce in a stream of hydrogen at 200° C. for 6 hours.

The results of three of the foregoing examples using a catalyst prepared as in Example 10, Method A were compared with the results of three examples illustrating the process of this invention using a catalyst containing spinel structures of zinc and aluminum. Details of the comparison which was made on the basis of similar reaction shell temperatures and NTP contact times are shown in Table III.

TABLE III

| Examples | Catalyst | Reactor Shell Temp. °C. | NTP Contact Time - Sec. | Methanol Conversion % | % Methanol To Methyl Formate Efficiency | Methyl Formate Yield % |
|---|---|---|---|---|---|---|
| 16 | $CuZn_{0.3}Zr_{0.3}Al_{0.1}$ | 300 | 1.4 | 20 | 59 | 12 |
| 8 | $Cu_6Zn_{2.9}Al_{1.4}$ | 297 | 1.4 | 41.5 | 63 | 26 |
| 17 | $CuZn_{0.3}Zr_{0.3}Al_{0.1}$ | 300 | 0.7 | 12 | 77 | 9 |
| 5 | $Cu_6Zn_{2.9}Al_{1.4}$ | 303 | 0.7 | 43.4 | 79 | 34 |
| 19 | $CuZn_{0.3}Zr_{0.3}Al_{0.1}$ | 280 | 1.4 | 13 | 77 | 10 |
| 6 | $Cu_6Zn_{2.9}Al_{1.4}$ | 279 | 1.4 | 36.4 | 88 | 32 |

In the above comparisons, the catalyst of the present invention Examples 5, 6 and 8 provided higher methanol conversions, methyl formate efficiencies and methyl formate yield than the catalyst made by Method A in Example 10 used in the process described in British Pat. No. 1,546,004 identified as Examples 16, 17 and 19.

EXAMPLES 21 THROUGH 26

The catalyst of Method B, Example 10 having the structure $CuZn_{0.3}Zr_{0.3}Al_{0.1}$ was placed in the same equipment and the same procedure was used as described in Examples 1 through 9 to produce methyl formate from methanol. Table IV describes the conditions and results of the methanol dehydrogenation process.

TABLE IV

Dehydrogenation of Methanol to Methyl Formate
$Cu_1Zr_{0.3}Zn_{0.3}Al_{0.1}$ - 9.9 Grams

| Examples | Reactor Shell Temp. °C. | Methanol Feed Grams | Product Grams | Product Methyl Formate Wt. % | Total Vent Gas ml. | $H_2$ Produced Mole % | CO Produced Mole % | NTP Contact Time Sec. | Methanol Conversion % | % Methanol to Methyl Formate Efficiency | % Methyl Formate Yield | Space Time Yield Grams Product Per Liter Space Per Hour |
|---|---|---|---|---|---|---|---|---|---|---|---|---|
| 21 | 280 | 22.1 | 18.9 | 29.5 | 8260 | 87.2 | 12.2 | 0.7 | 35 | 82 | 29 | 1572 |
| 22 | 255 | 23.7 | 22.9 | 16.2 | 4140 | 92.2 | 7.1 | 0.7 | 19 | 91 | 17 | 976 |
| 23 | 305 | 23.7 | 18.7 | 39.8 | 12510 | 83.6 | 15.7 | 0.7 | 48 | 76 | 37 | 1959 |
| 24 | 330 | 23.7 | 16.8 | 42.6 | 21240 | 74.4 | 24.9 | 0.7 | 60 | 53 | 32 | 1884 |
| 25 | 305 | 47.4 | 43.0 | 28.5 | 17490 | 80.0 | 19.3 | 0.35 | 36 | 75 | 27 | 3225 |
| 26 | 280 | 47.4 | 44.8 | 16.5 | 10008 | 87.6 | 11.9 | 0.35 | 18 | 83 | 15 | 1946 |

The results of two of the foregoing examples using a catalyst prepared as in Example 10, Method B were compared with the results of two examples illustrating the process of this invention using a catalyst containing spinel structures of zinc and aluminum. Details of the comparison which was made on the basis of the employment of similar reaction shell temperatures and the same NTP contact time, are shown in Table V.

TABLE V

| Example | Catalyst | Reactor Shell Temp. °C. | NTP Contact Time - Sec. | Methanol Conversion % | % Methanol To Methyl Formate Efficiency | Methyl Formate Yield % |
|---|---|---|---|---|---|---|
| 23 | $CuZn_{0.3}Zr_{0.3}Al_{0.1}$ | 305 | 0.7 | 48 | 76 | 37 |
| 5 | $Cu_6Zn_{2.9}Al_{1.4}$ | 303 | 0.7 | 43 | 79 | 34 |
| 21 | $CuZn_{0.3}Zr_{0.3}Al_{0.1}$ | 280 | 0.7 | 35 | 82 | 29 |
| 4 | $Cn_6Zn_{2.9}Al_{1.4}$ | 287 | 0.7 | 34.9 | 85 | 30 |

As compared with prior art Example 23, Example 5 illustrating the process of the invention and carried out at a similar reaction temperature, resulted in a lower methanol conversion but a higher efficiency of methanol to methyl formate. On the other hand, Example 4 illustrating the process of the invention at a higher temperature (287° C.) as compared to prior art Example 21 carried out at a temperature of 280° C., yielded a similar methanol conversion but a higher efficiency to methyl formate.

EXAMPLES 27 THROUGH 34

A catalyst having a metal atomic ratio of $CuZn_{0.1}Zr_{0.3}Al_{0.1}$ was prepared using the procedure of Example 10, Method A except that only one third the amount of zinc was used in the preparation relative to the other metals as is shown in the description of Example 10. This catalyst is shown in Table II of British Pat. No. 1,546,004. The catalyst was placed in the same equipment and the same procedure was used as described in Examples 1 through 9 to produce methyl formate from methanol. Table VI describes the conditions and results of the methanol dehydrogenation process.

TABLE VI

Dehydrogenation of Methanol to Methyl Formate
$Cu_1Zn_{0.1}Zr_{0.3}Al_{0.1}$ - 10.2 Grams

| Examples | Reactor Shell Temp. °C. | Methanol Feed Grams | Product Grams | Product Methyl Formate Wt. % | Total Vent Gas ml. | $H_2$ Produced Mole % | CO Produced Mole % | NTP Contact Time Sec. | Methanol Conversion % | % Methanol to Methyl Formate Efficiency | % Methyl Formate Yield | Space Time Yield Grams Product Per Liter Space Per Hour |
|---|---|---|---|---|---|---|---|---|---|---|---|---|
| 27 | 256 | 26.1 | 24.2 | 25.5 | 7293 | 92.1 | 6.5 | 0.7 | 30 | 91 | 27 | 1477 |
| 28 | 280 | 31.6 | 28.3 | 27.3 | 10600 | 87.4 | 10.9 | 0.7 | 32 | 85 | 27 | 1525 |
| 29 | 305 | 26.9 | 22.3 | 37.0 | 13634 | 82.3 | 16.2 | 0.7 | 45 | 75 | 34 | 1916 |
| 30 | 335 | 26.1 | 19.9 | 43.9 | 19437 | 75.7 | 23.1 | 0.7 | 58 | 61 | 35 | 2090 |
| 31 | 300 | 31.6 | 28.9 | 23.4 | 11780 | 81.1 | 17.7 | 0.35 | 31 | 73 | 23 | 2670 |
| 32 | 280 | 33.2 | 31.1 | 18.3 | 8400 | 85.1 | 14.0 | 0.35 | 23 | 80 | 18 | 2140 |
| 33 | 330 | 31.6 | 27.6 | 29.5 | 15000 | 80.5 | 18.6 | 0.35 | 39 | 70 | 27 | 3214 |
| 34 | 350 | 31.6 | 25.5 | 33.0 | 17840 | 78.5 | 20.6 | 0.35 | 45 | 65 | 29 | 3322 |

The results of prior art Example 29 shown in Table VI were compared with those of Example 5 illustrating the process of this invention using a catalyst containing spinel structures of zinc and aluminum. Details of the comparison which was based on the employment of similar reaction shell temperatures and the same NTP contact time, are shown in Table VII.

TABLE VII

| Examples | Catalyst | Reactor Shell Temp. °C. | NTP Contact Time-Sec. | Methanol Conversion % | % Methanol To Methyl Formate Efficiency | Methyl Formate Yield % |
|---|---|---|---|---|---|---|
| 29 | $CuZn_{0.1}Zr_{0.3}Al_{0.1}$ | 305 | 0.7 | 45 | 75 | 34 |
| 5 | $Cu_6Zn_{2.9}Al_{1.4}$ | 303 | 0.7 | 43.4 | 79 | 34 |

As shown in Table VII, the efficiency to methyl formate obtained in Example 5 is slightly higher than that obtained in prior art Example 29.

The comparative results shown in Tables III, V and VII indicate that superior or equivalent results are obtained using the process of this invention as compared with that disclosed by British Pat. No. 1,546,004 despite the fact that unlike the catalysts required by the latter process, the catalysts employed by the process claimed herein need not contain any metal of Groups IIIA or IVA as set forth in the periodic table given in "Elements of Physical Chemistry" by Samuel Glasstone, published by D. Van Nostrand Company (1946).

What is claimed is:

1. A process for producing methyl formate by the vapor phase dehydrogenation of methanol at temperatures of at least about 235° C. and at atmospheric or reduced pressures, by passing methanol over a catalyst produced by reducing with hydrogen a catalyst precursor comprising copper oxide in an amount such that said precursor comprises about 10 to about 80 weight percent copper based on the total metal atoms present, with the balance essentially a spinel structure support comprising the oxides of zinc and aluminum, said precursor being characterized by the presence of spinel in crystallites no greater than 120 Angstrom units.

2. The process of claim 1 wherein the dehydrogenation temperatures are about 235° C. to about 350° C.

3. The process of claim 2 wherein the spinel structure in the catalyst precursor is present as crystallites no greater than 80 Angstrom units in size.

4. The process of claim 2 wherein the catalyst precursor contains copper oxide crystallites no greater than 120 Angstrom units in size.

5. The process of claim 2 wherein the catalyst precursor contains copper oxide crystallites no greater than 70 Angstrom units in size.

6. The process of claim 1 wherein the copper oxide is present in an amount such that the precursor catalyst is about 25 to about 70 weight percent copper of the total metal atoms, the total zinc content is about 0.3 to about 0.6 of the copper content based on metal atoms and the remaining metal is aluminum.

7. A process for producing methyl formate by the vapor phase dehydrogenation of methanol at conversions from about 20 to about 60 percent and at temperatures from about 250° C. to about 320° C. at atmospheric pressure by passing methanol over a catalyst produced by reducing with hydrogen, a catalyst precursor containing metallic elements comprising copper oxide being present in an amount such that said precursor is present in an amount of about 25 to about 70 weight percent copper based on the total metal atoms present, zinc in an amount of about 0.3 to about 0.6 of the copper content based on metal atoms and the remainder aluminum, said precursor being in the form of oxides characterized by the presence of spinel in crystallite sizes of from about 30 to about 40 Angstrom units, and copper oxide in the form of crystallites no greater than 70 Angstrom units.

* * * * *